United States Patent
Stack et al.

(10) Patent No.: US 6,750,364 B2
(45) Date of Patent: Jun. 15, 2004

(54) BRIDGED TRICYCLIC ANALOGS OF 2-(CARBOXYCYCLOPROPYL)GLYCINE AS INHIBITORS OF GLUTAMATE TRANSPORT

(75) Inventors: Gary Paul Stack, Ambler, PA (US); John Dunlop, Allentown, NJ (US); Alexander Alexei Greenfield, Princeton Junction, NJ (US); Jonathan Laird Gross, Robbinsville, NJ (US)

(73) Assignee: Wyeth, Madison, NJ (US)

( * ) Notice: Subject to any disclaimer, the term of this patent is extended or adjusted under 35 U.S.C. 154(b) by 34 days.

(21) Appl. No.: 10/185,489

(22) Filed: Jun. 27, 2002

(65) Prior Publication Data

US 2003/0022930 A1 Jan. 30, 2003

Related U.S. Application Data

(60) Provisional application No. 60/302,251, filed on Jun. 29, 2001.

(51) Int. Cl.[7] .................. C07D 311/78; C07C 69/74
(52) U.S. Cl. .................. 560/117; 549/386; 562/499; 514/454; 514/530; 514/531
(58) Field of Search .............. 560/117; 562/499; 549/386; 514/454, 530, 531

(56) References Cited

U.S. PATENT DOCUMENTS 6,124,361 A 9/2000 Chenard

FOREIGN PATENT DOCUMENTS

| EP | 0 363 994 A2 A3 | 4/1990 |
| EP | 0 363 994 B1 | 9/1993 |
| WO | WO 99/47490 | 9/1999 |

OTHER PUBLICATIONS

Arvid Carlsson et al., Int. Acad. Biomed. Drug. Rcs., 4, 118–129, (1993).
W. Danysz et al., Behavioural Pharmacology, 6, 455–474 (1995).
L. Fowden et al., Phytochemistry, 8, 437–443, (1969).
F. Tellier et al., Bioorganic & Medicinal Chemistry, 6, 195–208, (1998).
Peter K. Freeman et al., The Journal of Organic Chemistry, 33(6), 2211–2214, (1968).
Steven R. Hirsch et al., Pharmacology Biochemistry & Behavior, 56(4), 797–802, (1997).
Yasunori Hayashi et al., Br. J. Pharmacol., 107, 539–543 (1992).
E. Frittoli et al., Neuropharmacology, 33(6), 833–835, (1994).
A. Kozikowski et al., J. Med. Chem., 41, 1641–1650 (1998).
J. Monn et al., J. Med. Chem., 40, 528–537 (1997).
O. Manzoni et al., Molecular Pharmacology, 38(1), 1–6 (1990).
K. Alder et al., Chem. Ber., 93, 2271–2281 (1960).
H.P. Koch et al., Molecular Pharmacology, 56, 1095–1104 (1999).
R. Bridges et al., Neuroscience Letters, 174, 193–197 (1994).
R. Pellicciari et al., J. Med. Chem., 39, 2259–2269 (1996).
T. Poll et al., Tetrahedron Letters, 30(41), 5595–5598 (1989).
M. Campbell et al., Tetrahedron, 40(13), 2461–2470 (1984).

*Primary Examiner*—Paul J. Killos
(74) *Attorney, Agent, or Firm*—Rebecca R. Barrett; Kimberly R. Hild

(57) ABSTRACT

This invention provides compounds of the formula:

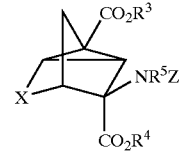

wherein X is $(CH_2)_n$, O, S, SO, $SO_2$ or $CR^1R^2$; n is 1 or 2; $R^1$ and $R^2$ are H, halogen, hydroxy, alkyl of 1 to 6 carbon atoms, alkoxy of 1 to 6 carbon atoms, or $R^1$ and $R^2$, taken together form cycloalkyl of 3 to 6 carbon atoms, an alkylidene of up to 6 carbon atoms or a carbonyl; $R^3$, $R^4$ and $R^5$ are H or alkyl of 1 to 6 carbon atoms; Z is H, alkyl of 1 to 6 carbon atoms, alkanoyl of 1 to 6 carbon atoms or alkoxycarbonyl of 2 to 7 carbon atoms; or a pharmaceutically acceptable salt thereof, as well as pharmaceutical compositions and methods for their use in treating or preventing characterized by glutamate hypofunction, including schizophrenia, schizoaffective disorder and schizophreniform disorder, and for the treatment of cognitive deficits due to aging, stroke, Alzheimer's disease or other neurodegenerative diseases.

18 Claims, No Drawings

BRIDGED TRICYCLIC ANALOGS OF 2-(CARBOXYCYCLOPROPYL)GLYCINE AS INHIBITORS OF GLUTAMATE TRANSPORT

This application claims priority from co-pending provisional application serial No. 60/302,251, filed on Jun. 29, 2001, the entire disclosure of which is hereby incorporated by reference.

This invention relates to bridged tricyclic analogs of 2-(carboxycyclopropyl)glycine as inhibitors of glutamate transport, to processes for preparing them and to pharmaceutical compositions containing them. The novel compounds of the invention are useful in the treatment of disorders associated with brain glutamate hypofunction in a mammal. The invention particularly provides compounds which are useful in the treatment, prevention, alleviation or inhibition of maladies including schizophrenia, schizoaffective disorder and schizophreniform disorder, and for the treatment of cognitive deficits due to aging, stroke, Alzheimer's disease or other neurodegenerative diseases.

BACKGROUND OF THE INVENTION 2-(carboxycyclopropyl)glycines (CCG's) are conformationally restricted glutamate analogs and consist of eight isomers including L- and D-enantiomers. L-CCG-I, [(2S, 3S,4S-CCG] isolated by Fowden et al. (Phytochemistry 1969, 8, 437) from immature fruits of *Aesculus parviflora* and *Blighia sapida* has been shown (Br. J. Pharmacol. 1992, 107, 539) to be a potent agonist for type 2 metabotropic glutamate receptors (mGluR2). L-CCG-III [(2S,3S,4R)-CCG], on the other hand, is a potent and competitive inhibitor of both glial and neuronal uptake of glutamate (Neuropharmacology 32, 833). EP0363994 claims the preparation of (2R,3S,4S)-alpha-(carboxycyclopropyl)glycine

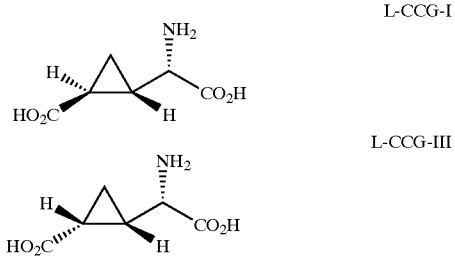

as an N-methyl-D-aspartic acid (NMDA) agonist useful as a tool to investigate various neuronal functions related to the excitatory amino acid receptors.

Bioorganic and Medicinal Chemistry 6 (1998) 195 describes the synthesis and pharmacological activity of a series of aminobicyclo[2.2.1]heptane dicarboxylic acids (ABHD's) as rigid analogs of 1-amino-cyclopentane-trans-1,3-dicarboxylic acid (trans-ACPD). 2-endo-Aminobicyclo[2.2.1]heptane-2-exo-7-anti-dicarboxylic acid (ABHD-I) is described as a competitive antagonist at the 1a subtype of the metabotropic glutamate receptor with a $K_b$ of 300 μM. Both ABHD-I and ABHD-II (2-exo-aminobicyclo[2.2.1]-heptane-2-endo-7-anti-dicarboxylic acid):

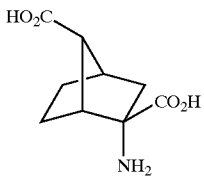

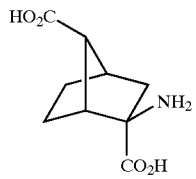

are characterized as agonists at type 2 mGluR's. Neither compound has significant activity at glutamate transporters.

Literature from Tocris Cookson lists two isomers of aminotricyclo-[2.2.1.0$^{2,6}$]heptane-dicarboxylic acid. 3-Exo-aminotricyclo[2.2.1.0$^{2,6}$]heptane-3-endo-7-anti-dicarboxylic acid (designated below as ATHD-I) is described as a weak agonist at type 2 metabotropic glutamate receptors. The activity of 3-endo-aminotricyclo-[2.2.1.0$^{2,6}$]heptane-3-exo-7-anti-dicarboxylic acid (designated ATHD-II) is said to

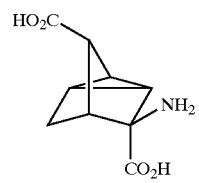

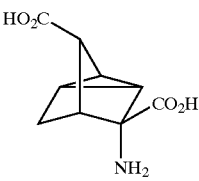

have not yet been established. No information on these compounds is available in the chemical or pharmacological literature. It should be noted that these compounds, while conformationally restricted analogs of trans-ACPD, are not analogs of 2-(carboxycyclopropyl)glycine. Furthermore, these compounds have no significant effect on glutamate transport.

WO 9947490 claims a series of compounds described by the formula below in which n is 0–6, X is $CH_2$, $CH_2CH$ or O, Z is $CHR^2$ or $NR^2$ and $R^1$ and $R^2$ are hydrogen, alkyl, aryl or heteroaryl as metabotropic glutamate receptor ligands useful for the treatment of a variety of neurological and psychiatric disorders.

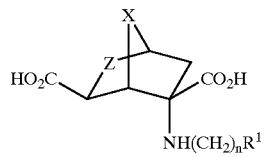

U.S. Pat. No. 6,124,361 (Chenard) teaches substituted bicyclo[3.1.0]hexane compounds of the formula:

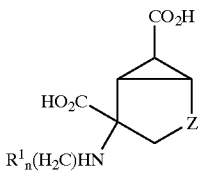

wherein n is an integer from 0 to 6; Z is $(C_1-C_4)$ alkylene, oxygen, sulfur, NH or $N(C_1-C_6)$alkyl; and $R^1$ is H or optionally substituted aryl or heteroaryl; which are metabotropic glutamate receptor ligands useful in the treatment of a variety of neurological and psychiatric disorders.

DESCRIPTION OF THE INVENTION

This invention provides a group of novel bridged tricyclic analogs of 2-(carboxy-cyclopropyl)glycine of the formula:

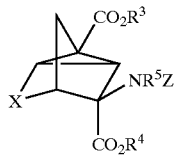

wherein:

X is $(CH_2)_n$, O, S, SO, $SO_2$ or $CR^1R^2$;

n is 1 or 2;

$R^1$ and $R^2$ are, independently, hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;

$R^3$, $R^4$ and $R^5$ are, independently, hydrogen or alkyl of one to six carbon atoms;

Z is hydrogen, alkyl of one to six carbon atoms, alkanoyl of one to six carbon atoms or alkoxycarbonyl of two to seven carbon atoms;

or a pharmaceutically acceptable salt thereof.

In a preferred embodiment of the invention, X is $(CH_2)_n$, O or $CR^1R^2$. More preferably, X is $(CH_2)_n$. Most preferably, n is 1.

In a further preferred embodiment of the invention, $R^1$ and $R^2$ are independently selected from hydrogen, methyl, chloro, bromo, hydroxy and methoxy.

In a still further preferred embodiment of the invention, $R^3$, $R^4$ and $R^5$ are hydrogen.

In a still further preferred embodiment of the invention, Z is hydrogen or alkyl of 1 to 6 carbon atoms. More preferably, Z is hydrogen.

A preferred group of compounds of this invention are those in which $R^1$, $R^2$ and n are defined as above, X is $(CH_2)_n$, O or $CR^1R^2$, $R^3$, $R^4$ and $R^5$ are hydrogen and Z is hydrogen or alkyl of one to six carbon atoms. Most preferred are those examples in which n is defined as above, X is $(CH_2)_n$, O or $CR^1R^2$, wherein $R^1$ and $R^2$ are, independently, hydrogen, halogen, hydroxy, alkyl of one to six carbon atoms or alkoxy of one to six carbon atoms and $R^3$, $R^4$, $R^5$ and Z are hydrogen.

One group of this invention includes compounds of the formulae:

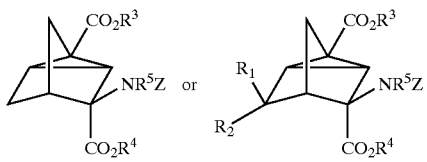

wherein:

$R^1$ and $R^2$ are independently selected from hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;

$R^3$, $R^4$ and $R^5$ are, independently, hydrogen or alkyl of one to six carbon atoms;

Z is hydrogen, alkyl of one to six carbon atoms, alkanoyl of one to six carbon atoms or alkoxycarbonyl of two to seven carbon atoms;

or a pharmaceutically acceptable salt thereof.

A subgroup of compounds of those above have the formulae:

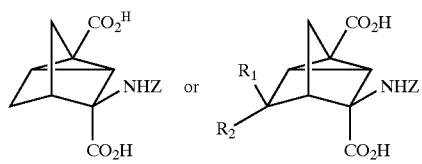

wherein:

Z is H or alkyl of from 1 to 6 carbon atoms; and $R_1$ and $R_2$ are independently selected from H, halogen, hydroxy, alkyl of from 1 to 6 carbon atoms or alkoxy of from 1 to 6 carbon atoms;

or a pharmaceutically acceptable salt thereof.

Representative compounds of this invention wherein X is $(CH_2)_n$ or $CR^1R^2$ include, but are not limited to:

3-Amino-tricyclo[2.2.1.0$^{2,6}$]heptane-1,3-dicarboxylic acid;

3-Methylamino-tricyclo[2.2.1.0$^{2,6}$]heptane-1,3-dicarboxylic acid;

3-Ethylamino-tricyclo[2.2.1.0$^{2,6}$]heptane-1,3-dicarboxylic acid;

3-Amino-5-methyl-tricyclo[2.2.1.0$^{2,6}$]heptane-1,3-dicarboxylic acid;

3-Amino-5-chloro-tricyclo[2.2.1.0$^{2,6}$]heptane-1,3-dicarboxylic acid;

3-Amino-5-bromo-tricyclo[2.2.1.0$^{2,6}$]heptane-1,3-dicarboxylic acid;

3-Amino-5,5-dichloro-tricyclo[2.2.1.0$^{2,6}$]heptane-1,3-dicarboxylic acid;

3-Amino-5,5-dimethyl-tricyclo[2.2.1.0$^{2,6}$]heptane-1,3-dicarboxylic acid;

5,5-Dimethyl-3-methylamino-tricyclo[2.2.1.0$^{2,6}$]heptane-1,3-dicarboxylic acid;

5-Hydroxy-3-methylamino-tricyclo[2.2.1.0$^{2,6}$]heptane-1,3-dicarboxylic acid;

3-Amino-5-methoxy-tricyclo[2.2.1.0$^{2,6}$]heptane-1,3-dicarboxylic acid;

5-Methoxy-3-methylamino-tricyclo[2.2.1.0$^{2,6}$]heptane-1,3-dicarboxylic acid;

or a pharmaceutically acceptable salt thereof.

Another group of compounds of this invention comprises those of the formula:

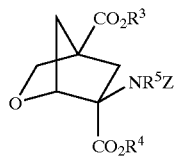

wherein:
R³, R⁴ and R⁵ are independently selected from hydrogen or alkyl of one to six carbon atoms; and
Z is hydrogen, alkyl of one to six carbon atoms, alkanoyl of one to six carbon atoms or alkoxycarbonyl of two to seven carbon atoms;
or a pharmaceutically acceptable salt thereof.

A further group of these compounds are those of the formula:

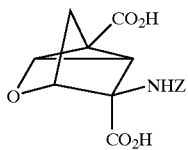

wherein Z is selected from H or alkyl of from 1 to 6 carbon atoms; or a pharmaceutically acceptable salt thereof.

This invention relates to both enantiomers and diastereomers of the bridged tricyclic aminodicarboxylic acids described above, as well as to mixtures of the enantiomers and diastereomers. Throughout this application, the name of the product of this invention, where the absolute configuration or the optical rotation of the bridged tricyclic aminodicarboxylic acid is not indicated, is intended to embrace the individual enantiomers as well as mixtures of the two. When it is necessary to distinguish the enantiomers from one another and from the racemate, the sign of the optical rotation [(+), (−) and (+/−)] is utilized. Furthermore, throughout this application, the designations R* and S* are used to indicate relative stereochemistry, employing the Chemical Abstracts convention which automatically assigns R* to the lowest numbered asymmetric center. While the above genus is intended to embrace both diastereomers about the amino acid α-carbon, the R* configuration is preferred.

It will be understood that each of the stereoisomers of this invention may be separated and utilized substantially free of their corresponding stereoisomer. Within the scope of this invention, each compound is considered substantially free of its corresponding stereoisomer when the final product comprises greater than 95% of the desired compound, more preferably greater than 98%, even more preferably greater than 99.9%.

Alkyl as used herein refers to an aliphatic hydrocarbon chain and includes straight and branched chains such as methyl, ethyl, n-propyl, n-butyl, isobutyl, sec-butyl, t-butyl, n-pentyl, isopentyl, neopentyl, n-hexyl and isohexyl.

Halogen (or halo) as used herein refers to chlorine, bromine, fluorine and iodine.

Alkoxy as used herein refers to the group R—O— where R is an alkyl group of 1 to 6 carbon atoms.

Alkylidene as used herein refers to the group R⁶R⁷C═C where R⁶ and R⁷ are independently hydrogen or alkyl groups of 1 to 5 carbon atoms, the group having from 2 to 6 carbon atoms.

Alkanoyl as used herein refers to the group R—C(═O)— where R is hydrogen or an alkyl group of 1 to 5 carbon atoms.

Alkoxycarbonyl as used herein refers to the group R—O—C(═O)— where R is an alkyl group of from 1 to 5 carbon atoms.

The pharmaceutically acceptable salts are those derived from such organic and inorganic acids as: acetic, lactic, citric, tartaric, succinic, fumaric, maleic, malonic, mandelic, mallic, hydrochloric, hydrobromic, phosphoric, nitric, sulfuric, methane-sulfonic, toluenesulfonic and similarly known acceptable acids. Alternatively, the compounds of the invention which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di- and trimethylammonium, mono-, di- and triethylammonium, mono-, di-, and tripropyl-ammonium (iso and normal), ethyidimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methyl-piperidinium, 1-ethyl-2-methylpiperidinium, mono-, di- and triethanolammonium, ethyl diethanolammonium, n-butylmonoethanolammonium, tris(hydroxymethyl)methyl-ammonium, phenylmonoethanolammonium, and the like.

The bridged tricyclic aminodicarboxylic acids of the invention are prepared as illustrated below. Specifically, the appropriately substituted cyclic diene is caused to undergo a Diels-Alder reaction with α-chloroacrylonitrile by refluxing in a suitable solvent such as benzene or toluene to give the bicyclic α-chloronitrile as a mixture of diastereomers. Hydrolysis of the α-chloronitrile with potassium hydroxide in a mixture of ethanol and water is accompanied by participation of the double bond and yields a bridged tricyclic hydroxy acid. The carboxylic acid moiety is esterified, for example by treatment with

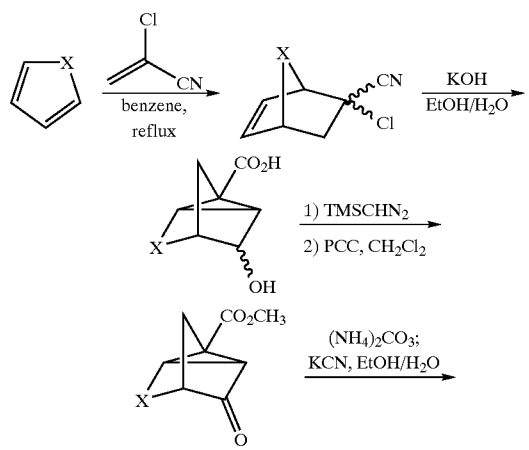

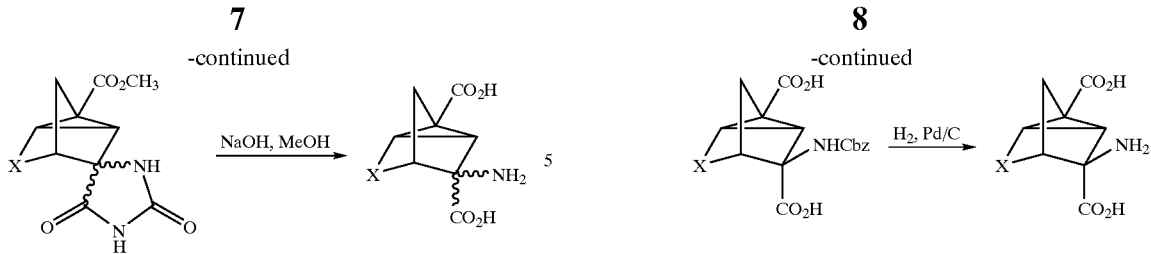

trimethylsilyldiazomethane, and the hydroxy group converted to the carbonyl by treatment with a suitable oxidant such as pyridinium chlorochromate (PCC) or the Swern reagent. The resulting keto ester is then subjected to the classical Bucherer-Bergs conditions (ammonium carbonate and an alkali metal cyanide, such as potassium cyanide, in ethanol/water) to give a spiro-fused hydantoin as a mixture of diastereomers. Hydrolysis of the hydantoin and the ester moieties in either acid or base followed by purification of the crude product by ion exchange chromatography gives the title compounds of the invention, which may contain varying amounts of two diastereomers about the amino acid α-carbon. The ammonium carbonate and alkali metal cyanide compounds of this step may be used at concentrations known in the art, such as a concentration from about 0.1M to the saturation point of the compound in the reaction medium. A more preferable concentration would be from about 0.5M to about 3M.

Alternatively, the diastereomers of the aminodicarboxylic acids may be conveniently separated by the procedure outlined below. The crude mixture of diastereomeric aminodicarboxylic acids is converted to methyl esters by a suitable esterification procedure, such as treatment with thionyl chloride in methanol. The amino group is then functionalized under standard conditions with a suitable protecting group such carbobenzoxy (Cbz), which provides a convenient chromophore for the identification of the products on thin layer and column chromatography. The fully protected diastereomeric aminodicarboxylic acids are separated by column chromatography on silica gel and the title compounds of the invention isolated following ester hydrolysis in base and hydrogenolysis of the carbobenzoxy group with hydrogen over palladium on carbon.

The compounds of the invention may alternatively be derived by the procedure outlined below, in which a known unsaturated bicyclic ester or nitrile is epoxidized by a suitable reagent such as meta-chloroperoxybenzoic acid (m-CPBA) and the epoxide caused to react with the anion of the ester or nitrile via treatment with a suitable base such as potassium hexamethyldisilazide to give the hydroxy nitrile or the hydroxy ester described above. Or the known unsaturated bicyclic ester or nitrile may be converted to the vicinal diol by treatment with N-methylmorpholine oxide and catalytic osmium tetroxide and thence to the cyclic sulfate according to the procedure of Sharpless, i.e. treatment with thionyl chloride and a tertiary base, followed by oxidation with ruthenium tetroxide. Deprotonation of the ester or nitrile with a strong base such as potassium hexamethyldisilazide causes an intramolecular alkylation which, after hydrolysis of the intermediate sulfate in acid, gives the hydroxy nitrile or the hydroxy ester described above.

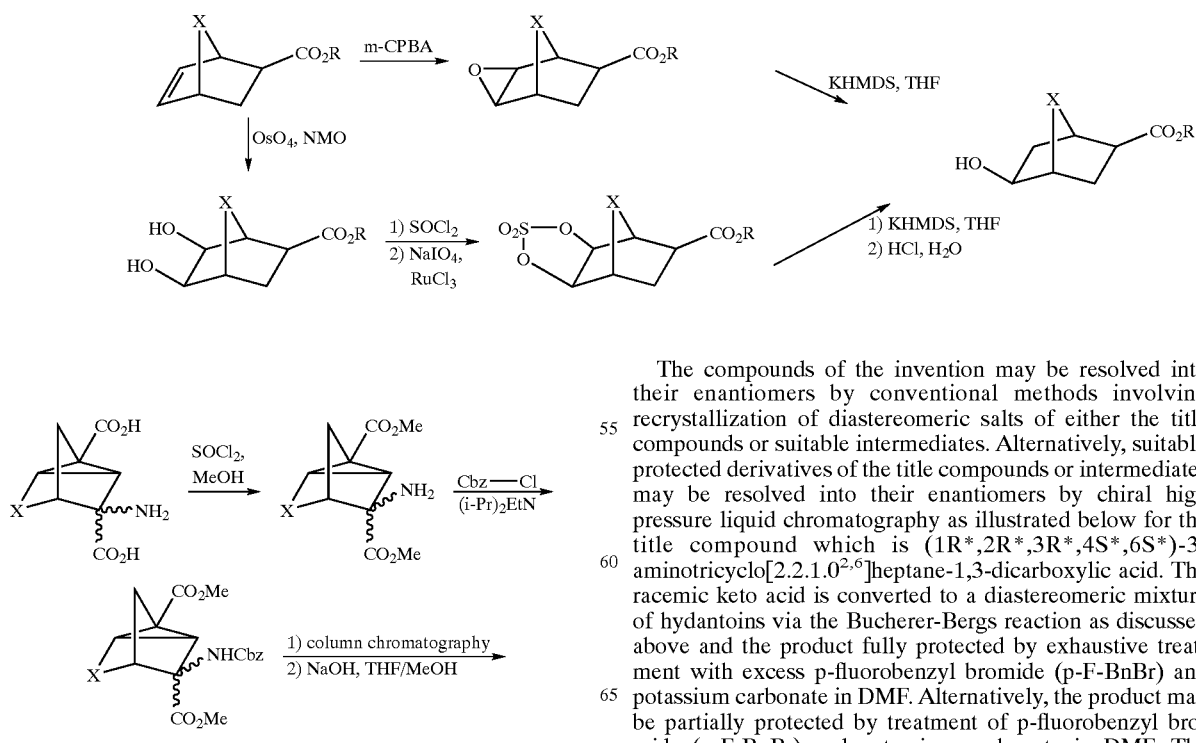

The compounds of the invention may be resolved into their enantiomers by conventional methods involving recrystallization of diastereomeric salts of either the title compounds or suitable intermediates. Alternatively, suitably protected derivatives of the title compounds or intermediates may be resolved into their enantiomers by chiral high pressure liquid chromatography as illustrated below for the title compound which is (1R*,2R*,3R*,4S*,6S*)-3-aminotricyclo[2.2.1.0$^{2,6}$]heptane-1,3-dicarboxylic acid. The racemic keto acid is converted to a diastereomeric mixture of hydantoins via the Bucherer-Bergs reaction as discussed above and the product fully protected by exhaustive treatment with excess p-fluorobenzyl bromide (p-F-BnBr) and potassium carbonate in DMF. Alternatively, the product may be partially protected by treatment of p-fluorobenzyl bromide (p-F-BnBr) and potassium carbonate in DMF. The diastereomers are separated by column chromatography on silica gel and the diastereomer appropriate to the preferred (3R*)-α-amino acid submitted to an additional chromatography on a chiral Whelk-O column or AD-chiralcel as appropriate. The individual enantiomers are separately deprotected by successive treatment with 2.5 N sodium hydroxide at elevated temperature and hydrogenolysis over palladium on carbon to provide the dextro- and levorotatory forms of the title compound.

non-racemic form. Since all of the chemistry detailed above is either stereospecific or, like the Bucherer-Bergs, gives separable mixtures of diastereomers, the individual enantiomers of the compounds of the invention may be prepared stereoselectively from the individual enantiomers of the starting materials. Furthermore, the absolute stereochemistry of the product may be inferred from the known absolute stereochemistry of the starting material. For example, the enantiomers of 5-norbornene-2-carboxylic acid are known,

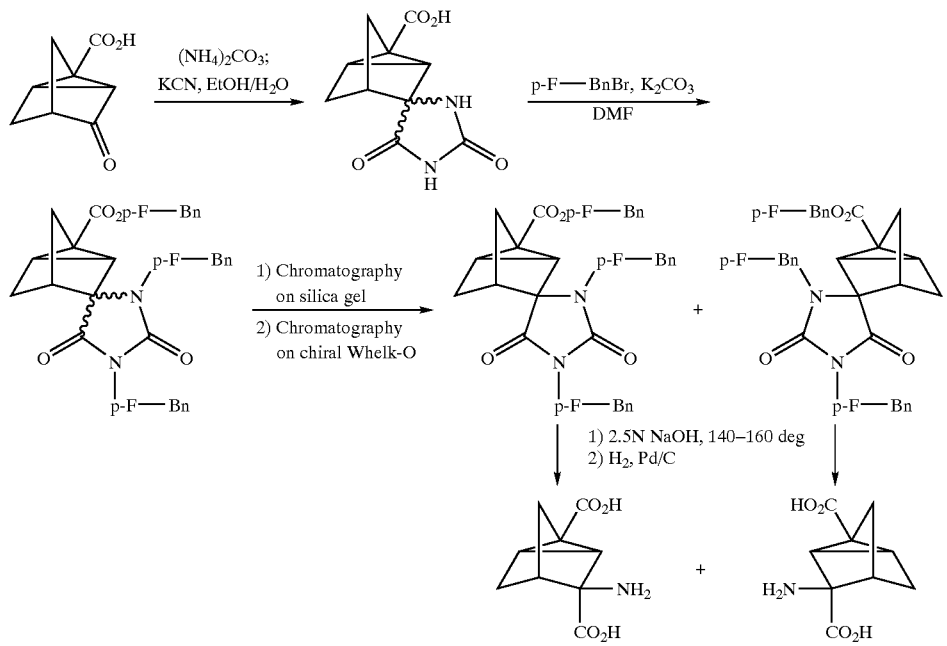

Mixtures of diastereomers and enatiomers may also be resolved according to the following scheme in which a racemic keto acid is reacted with a chiral alcohol or chiral amine and the diastereomer separated by reverse phase chromatography on a Welk-O column. Thereafter, separated diastereomers are converted to hydantoins via the Bucherer-Bergs reaction. The hydantoins are treated with a base and the stereoisomers eluted on an ion exchange column.

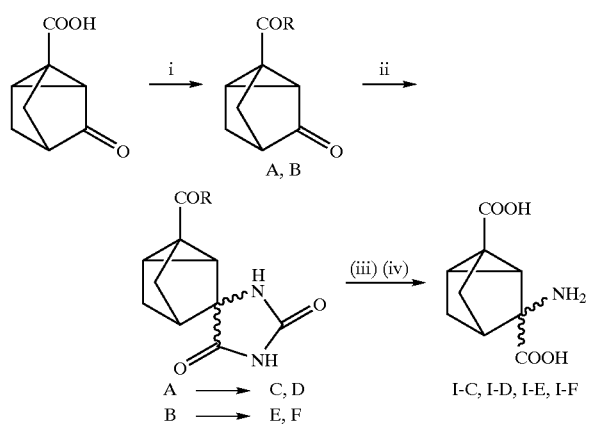

(i) TBTU, suitable chiral alcohol or amine, HPLC, (ii) KCN, ammonium carbonate, MeOH, water, HPLC, (iii) 2N NaOH, (iv) Ion exchange
Where R represents the residue of the chiral alcohol or amine Finally, the appropriate starting materials for some of the compounds of the invention are known or available in chiral and may be obtained in very high chiral purity either by resolution of a diastereomeric salt or, more conveniently, via an asymmetric Diels-Alder reaction.

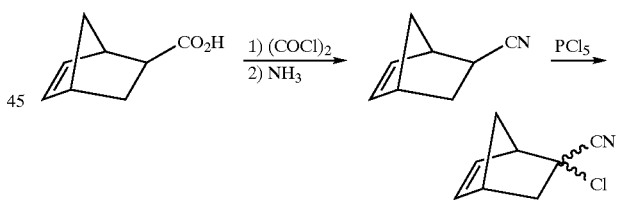

The 5-norbornene-2-carboxylic acid enantiomers may be converted to 3-aminotricyclo-[2.2.1.0$^{2,6}$]heptane-1,3-dicarboxylic acids via the epoxidation or bis-hydroxylation chemistry described above. More conservatively, the 5-norbornene-2-carboxylic acid enantiomers may be converted to the corresponding nitriles by standard methods, then alpha-chlorinated without rearrangement as described in J. Org. Chem. 33, 2211 (1968) to give the bicyclic α-chloronitrile precursor to the 3-aminotricyclo[2.2.1.0$^{2,6}$]-heptane-1,3-dicarboxylic acids described in the initial route above.

The compounds of the invention are selective inhibitors of human type 2 excitatory amino acid transporters (EAAT2). They thus serve to increase synaptic glutamate levels by inhibiting glutamate re-uptake and are useful for treatment of diseases characterized by glutamate hypofunction, such as schizophrenia, schizoaffective disorder and schizophreniform disorder (Int. Acad. Biomed. Drug Res. Basel, Karger, 1993, vol. 4, p. 118–129; Pharmacol., Biochem. Behav. (1997), 56(4), 797–802), with particular effectiveness against the negative symptoms of schizophrenia, and for the treatment of conditions which, though not necessarily caused by glutamate hypofunction, are nonetheless responsive to treatment by increased glutamate, such as the cognitive deficits due to aging, stroke, Alzheimer's disease or other neurodegenerative diseases, or schizophrenia (Behav. Pharmacol. (1995), Date 1995, Volume 6(5 & 6), 455–74). The compounds of the invention are especially useful as tools to investigate the contribution of glial excitatory amino transport to neuronal functions related to glutamatergic neurotransmission.

The effect of the compounds of the invention on EAAT2-mediated glutamate transport was established by examining their effects on L-[$^3$H]glutamate uptake into cells expressing the human EAAT2 subtype (MDCK/EAAT2). Cells were incubated at room temperature for 20 min in Dulbecco's phosphate buffered saline containing L-[$^3$H]glutamate, in the absence or presence of test compounds in the range 0.1–1000 μM. Uptake assays were stopped by aspiration followed by two rapid ice-cold washes and accumulated radioactivity was measured by scintillation counting. Inhibitor $IC_{50}$ values were estimated from log-concentration response curves by non-linear regression analysis.

The results of this testing with compounds representative of this invention, as well as standard compounds, are given below.

| Compound | EAAT2 Inhibition ($IC_{50}$ (μM)) |
| --- | --- |
| Example 1 | 2.4 |
| Example 2 | 114.5 |
| Example 3 | 1.7 |
| Dihydrokainic acid | 14.7 |
| Kainic acid | 39.9 |
| L-CCG-III | 6.3 |

Hence, the compounds of this invention have potent and selective inhibitory effect on human EAAT2. This invention comprises methods for the treatment, prevention, inhibition or alleviation of diseases associated with brain glutamate hypofunction in a mammal in need of such medical assistance.

These treatments include those of disorders such as schizophrenia, schizoaffective disorder and schizophreniform disorder, which are characterized by glutamate hypofunction, and for the treatment of cognitive deficits due to aging, stroke, Alzheimer's disease or other neurodegenerative diseases, or schizophrenia. The compounds of the invention are especially useful as tools to investigate the contribution of glial excitatory amino transport to neuronal functions related to glutamatergic neurotransmission. This invention provides methods for treating, inhibiting, alleviating or preventing each of these maladies, disorders or conditions, each method comprising administering to a mammal in need thereof a pharmaceutically effective amount of one or more compounds of this invention, or a pharmaceutically acceptable salt thereof. Each method may be used to inhibit or prevent the onset of the disorder in question or to treat the symptoms of the disorder or lessen their severity.

This invention also comprises pharmaceutical compositions comprising a pharmaceutically or therapeutically effective amount of one or more compounds of this invention, or a pharmaceutically acceptable salt thereof, and one or more pharmaceutically acceptable excipients or carriers. A pharmaceutically or therapeutically effective amount of a compound or salt form herein is understood to be an amount of the compound in question which will provide a desired improvement, alleviation or diminution of the symptoms or underlying physiological basis of the malady in question. A pharmaceutically or therapeutically effective amount is also understood to be an amount which will inhibit or prevent the onset of symptoms or conditions of the disorder or malady in question.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis or cognitive deficit must be subjectively determined by the attending physician. The variables involved include the specific psychosis or cognitive deficit and the size, age and response pattern of the patient. It is preferred that the compounds of this invention be administered at a low initial dose, with the amount being increased gradually until the desired medical benefits are achieved. A starting dose of about 10 mg per day with gradual increase in the daily dose to about 200 mg per day is suggested for human administration. If needed, higher daily doses may be utilized, including daily dosages of up to about 400 mg. The compounds and pharmaceutical compositions of this invention may be administered as a single daily dosage or as multiple doses over the course of the day.

The following examples illustrate the production of representative compounds of this invention.

INTERMEDIATE 1

2', 5'-Dioxo-spiro{tricyclo[2.2.1.0$^{2,6}$]heptane-3,4'-imidazoline}-1-carboxylic acid methyl ester To a solution of 6.8 g (41 mmole) of methyl 3-oxo-tricyclo[2.2.1.0$^{2,6}$]heptane-1-carboxylate in 120 mL of 1:1 ethanol/water was added ammonium carbonate (17.3 g, 0.18 mole) and potassium cyanide (3.12 g, 48 mmole) and the mixture was heated at 55–60° C. for 24 hours. Dilution with 400 mL of water and filtration of the resulting precipitate gave 2.2 g of an ~80:20 mixture favoring the minor (3S*) diastereomer by thin layer chromatography. A pure sample of the minor diastereomer obtained by recrystallization from methanol gave m.p. 288–290° C.

Elemental Analysis for: $C_{11}H_{12}N_2O_4$
Calc'd: C, 55.93; H, 5.12; N, 11.86
Found: C, 55.76; H, 5.14; N, 11.47

The aqueous mother liquor from the procedure above was extracted with ethyl acetate (3×300 mL) and the combined extracts dried over sodium sulfate, filtered and concentrated in vacuum to yield 5.1 g of the major (3R*) diastereomer, which contain approximately 20% of the minor diastereomer. A pure sample of the major diastereomer was obtained by column chromatography on silica gel with 1:1 hexane/ethyl acetate and had m.p. 212–213° C.

Elemental Analysis for: $C_{11}H_{12}N_2O_4 \cdot 0.10\ H_2O$
Calc'd: C, 55.51; H, 5.17; N, 11.77
Found: C, 55.38; H, 5.02; N, 11.52

INTERMEDIATE 2

(1R*,2R*,3R*,4S*,6S*)-3-Benzyloxycarbonylamino-tricyclo[2.2.1.0$^{2,6}$]heptane-1,3-dicarboxylic acid dimethyl ester The major (3R*) diastereomer of 2',5'-dioxo-spiro{tricyclo[2.2.1.0$^{2,6}$]heptane-3,4'-imidazoline}-1-carboxylic acid methyl ester (2.0 g, 8.5 mmole) was treated at reflux with 100 mL of 3 N sodium hydroxide for 24 hours. Upon cooling to room temperature, the mixture was acidified to pH 3 with concentrated HCl and evaporated in vacuum to a white solid. The solid was suspended in 300 mL of methanol and cooled in an ice bath. Thionyl chloride (4.8 g, 40 mmole) was added dropwise over 30 minutes and the mixture refluxed for 48 hours. It was then filtered, concentrated in vacuum, re-suspended in 350 mL of methylene chloride and washed with 350 mL portions of saturated aqueous sodium bicarbonate and saturated brine. The solution was dried over sodium sulfate, filtered, concentrated in vacuum and column chromatographed on silica gel with chloroform as eluant to give 1.45 g of (+/−)-(1R*,2R*,3R*,4S*,6S*)-3-amino-tricyclo[2.2.1.0$^{2,6}$]heptane-1,3-dicarboxylic acid dimethyl ester. This was dissolved in 75 mL of methylene chloride and 1.3 g (10 mmole) of diisopropylethylamine and 1.7 g (10 mmole) of benzyl chloroformate added. The mixture was stirred for 2 hours at room temperature, diluted to 250 mL with methylene chloride, washed with 150 mL portions of 2 N aqueous HCl, saturated aqueous sodium bicarbonate and saturated brine, dried over sodium sulfate, filtered and concentrated in vacuum. Column chromatography on silica gel with 20% ethyl acetate/hexane gave 1.9 g of the title compound, followed by 0.47 g of the minor (3S*) diastereomer. Recrystallization of the title compound from ethyl acetate/hexane gave a white solid, m.p. 125–126° C.

Elemental Analysis for: $C_{19}H_{21}NO_6$
Calc'd: C, 63.50; H, 5.89; N, 3.90
Found: C, 63.31; H, 5.80; N, 3.70

INTERMEDIATE 3

(1R*,2R*,3R*,4S*,6S*)-3-Benzyloxycarbonylamino-tricyclo[2.2.1.0$^{2,6}$]heptane-1,3-dicarboxylic acid A suspension of 2.0 g (5.6 mmole) of (+/−)-(1R*,2R*,3R*,4S*,6S*)-3-benzyloxycarbonylamino-tricyclo[2.2.1.0$^{2,6}$]heptane-1,3-dicarboxylic acid dimethyl ester in a mixture of 30 mL of tetrahydrofuran and 30 mL of 1 N aqueous sodium hydroxide was stirred at room temperature for 24 hours. Because the starting material was unchanged, methanol was added until homogeneity was achieved and the solution was refluxed under nitrogen for 15 hours. The mixture was acidified with concentrated HCl and extracted with ethyl acetate (2×200 mL). The extract was washed with 200 mL portions of water and saturated brine, dried over sodium sulfate, filtered and concentrated in vacuum. The resulting residue was recrystallized from ethyl acetate/hexane to give 1.2 g of the title compound as a white solid, m.p. 205° C.

Elemental Analysis for: $C_{17}H_{17}NO_6$
Calc'd: C, 61.63; H, 5.17; N, 4.23
Found: C, 61.33; H, 5.44; N, 3.93

EXAMPLE 1

(1R*,2R*,3R*,4S*,6S*)-3-Amino-tricyclo[2.2.1.0$^{2,6}$]heptane-1,3-dicarboxylic acid To a solution of 1.1 g (3.3 mmole) of (+/−)-(1R*,2R*,3R*,4S*,6S*)-3-benzyloxycarbonylamino-tricyclo[2.2.1.0$^{2,6}$]heptane-1,3-dicarboxylic acid in 100 mL of 1:1 ethanol/water was added 0.25 g of 10% palladium on carbon. The mixture was treated with 60 psi of hydrogen on a Parr apparatus for 24 hours. The catalyst was removed by filtration through celite and the filtrate was concentrated in vacuum to give 0.18 g of the title compound as a gray solid sesquihydrate. Extraction of the catalyst and celite with boiling water, filtration of the extracts through a millipore filter and concentration in vacuum led to the isolation of an additional 0.32 g of white solid. This was recrystallized from water to give 0.21 g of the title compound as a white crystalline one-quarter hydrate, m.p.>250° C.

Elemental Analysis for: $C_9H_{11}NO_4 \cdot 0.25\ H_2O$
Calc'd: C, 53.60; H, 5.75; N, 6.94
Found: C, 53.29; H, 5.45; N, 6.86

INTERMEDIATE 4

(1R*,2R*,3S*,4S*,6S*)-3-Benzyloxycarbonylamino-tricyclo[2.2.1.0$^{2,6}$]heptane-1,3-dicarboxylic acid dimethyl ester The minor (3S*) diastereomer of 2',5'-dioxo-spiro{tricyclo[2.2.1.0$^{2,6}$]heptane-3,4'-imidazoline}-1- carboxylic acid methyl ester (2.0 g, 8.5 mmole) was treated at reflux with 100 mL of 3 N sodium hydroxide for 24 hours. Upon cooling to room temperature, the mixture was acidified to pH 3 with concentrated HCl and evaporated in vacuum to a white solid. The solid was suspended in 300 mL of methanol and cooled in an ice bath. Thionyl chloride (4.8 g, 40 mmole) was added dropwise over 30 minutes and the mixture refluxed for 48 hours. It was then filtered, concentrated in vacuum, re-suspended in 500 mL of methylene chloride and washed with 500 mL portions of saturated aqueous sodium bicarbonate and saturated brine. The solution was dried over sodium sulfate, filtered, concentrated in vacuum and column chromatographed on silica gel with chloroform as eluant to give 1.0 g of (+/−)-(1R*,2R*,3S*,4S*,6S*)-3-amino-tricyclo[2.2.1.0$^{2,6}$]heptane-1,3-dicarboxylic acid dimethyl ester. This was dissolved in 50 mL of methylene chloride and 1.3 g (10 mmole) of diisopropylethylamine and 1.0 g (6.0 mmole) of benzyl chloroformate added. The mixture was stirred for 2 hours at room temperature, diluted to 200 mL with methylene chloride, washed with 200 mL portions of 2 N aqueous HCl, saturated aqueous sodium bicarbonate and saturated brine, dried over sodium sulfate, filtered and concentrated in vacuum. Column chromatography on silica gel with 20% ethyl acetate/hexane gave first 0.33 g of the (3R*) diastereomer, followed by 1.2 g of the title compound. This was combined with 0.47 g from above and recrystallized from ethyl acetate/hexane to give 1.6 g of a white solid, m.p. 118° C.

Elemental Analysis for: $C_{19}H_{21}NO_6$
Calc'd: C, 63.50; H, 5.89; N, 3.90
Found: C, 63.32; H, 5.79; N, 3.84

INTERMEDIATE 5

(1R*,2R*,3S*,4S*,6S*)-3-Benzyloxycarbonylamino-tricyclo[2.2.1.0$^{2,6}$]heptane-1,3-dicarboxylic acid A suspension of 1.6 g (4.5 mmole) of (+/−)-(1R*,2R*,3S*,4S*,6S*)-3-benzyloxy-carbonylamino-tricyclo[2.2.1.0$^{2,6}$]heptane-1,3-dicarboxylic acid dimethyl ester in a mixture of 30 mL of tetrahydrofuran and 30 mL of 1 N aqueous sodium hydroxide was stirred at room temperature for 24 hours. Because the starting material was unchanged, methanol was added until homogeneity was achieved and the solution was refluxed under nitrogen for 15 hours. The mixture was then acidified with concentrated HCl to precipitate 1.1 g of the title compound as a white solid, m.p. 238–239° C.

Elemental Analysis for: $C_{17}H_{17}NO_6$
Calc'd: C, 61.63; H, 5.17; N, 4.23
Found: C, 61.48; H, 5.33; N, 3.94

EXAMPLE 2

(1R*,2R*,3S*,4S*,6S*)-3-Amino-tricyclo[2.2.1.0$^{2,6}$]heptane-1,3-dicarboxylic acid To a solution of 1.0 g (3.0 mmole) of (+/−)-(1R*,2R*,3S*,4S*,6S*)-3-benzyloxy-carbonylamino-tricyclo[2.2.1.0$^{2,6}$]heptane-1,3-dicarboxylic acid in 100 mL of 1:1 ethanol/water was added 0.25 g of 10% palladium on carbon. The mixture was treated with 60 psi of hydrogen on a Parr apparatus for 24 hours. The catalyst was removed by filtration through celite and the filtrate was concentrated in vacuum to give 0.16 g of the title compound as a gray solid, m.p.>280° C.

Elemental Analysis for: $C_9H_{11}NO_4.0.80\ H_2O$
Calc'd: C, 51.08; H, 6.00; N, 6.62
Found: C, 50.80; H, 5.46; N, 6.56

INTERMEDIATE 6

2',5'-Dioxo-spiro{tricyclo[2.2.1.0$^{2,6}$]heptane-3,4'-imidazoline}-1-carboxylic acid A mixture of 1.52 g (10 mmole) of 3-oxo-tricyclo[2.2.1.0$^{2,6}$]heptane-1-carboxylic acid, 0.78 g (12 mmole) of potassium cyanide and 3.36 g (35 mmole) of ammonium carbonate in 75 mL of ethanol-water (1:1) was stirred at 75° C. for 18 hours. An additional 2–4 mmole of potassium cyanide and 6–12 mmole of ammonium carbonate were added and stirring at 75° C. was continued for 18 hours. The ethanol was then allowed to evaporate and the reaction mixture adjusted to pH 1 with concentrated HCl. Upon cooling the mixture to 0° C., a white precipitate formed and was removed by filtration and washed with ice-cold water and ethyl acetate and dried in vacuum to give 1.32 g of the title compound. Concentration of the mother liquor led to the isolation of an additional 0.22 g of white solid. Thus, 1.54 g of the title compound were obtained as a mixture of diastereomers.

INTERMEDIATE 7

1',3'-di-(4-fluorobenzyl)-2',5'-dioxo-spiro{tricyclo[2.2.1.0$^{2,6}$]heptane-3,4'-imidazoline}-1-carboxylic acid 4-fluorobenzyl ester A solution of 1.1 g (5.0 mmole) of 2',5'-dioxo-spiro{tricyclo[2.2.1.0$^{2,6}$]heptane-3,4'-imidazoline}-1-carboxylic acid in 30 mL of N,N-dimethylformamide was treated with an excess of p-fluorobenzyl bromide (4.73 g, 25 mmole) and potassium carbonate (3.45 g, 25 mmole) at 60° C. for 36 hours. After cooling to room temperature, the mixture was diluted to 500 mL with water and extracted with 2×250 mL of ethyl acetate. The extracts were washed with water, dried over sodium sulfate and concentrated in vacuum to give 2.7 g of the title compound, again as a mixture of diastereomers.

A mixture of the diastereomers of 1',3'-di-(4-fluorobenzyl)-2',5'-dioxo-spiro{tricyclo[2.2.1.0$^{2,6}$]heptane-3,4'-imidazoline}-1-carboxylic acid 4-fluorobenzyl ester (6.7 g, material from several reactions) was chromatographed using HPLC (Primesphere 10 silica column, 50×250 mm, with 24% ethyl acetate/hexane as eluant at a flow rate of 95 mL/min) to give the individual diastereomers of the title compound, each as a racemic mixture. The major product, the precursor to the (3R*) amino acid, was the first to elute (retention time=12.1 minutes) and 3.0 g was obtained as a colorless foam upon concentration in vacuum. This was resolved into the individual enantiomers by chiral HPLC on a Whelk-O column (2×25 cm, 1:1 ethanol-hexane, 20 mL/min) and 1.5 g of each of the enantiomers was obtained upon evaporation of solvent.

EXAMPLE 3

(−)-(1R*,2R*,3R*,4S*,6S*)-3-Amino-tricyclo[2.2.1.0$^{2,6}$]heptane-1.3-dicarboxylic acid 1.1 g (2.0 mmole) of the first enantiomer (retention time=6.6 minutes on analytical Whelk-O with 50:50 ethyl acetate-hexane at 1 mL/min) to elute from the chiral HPLC chromatography described in the above procedure was subjected to a hydrolysis in a stirred mixture of 2.5 N NaOH (30 mL)-methanol (10 mL) in a stainless steel autoclave at 160° C. for 32 hours. After completion of the reaction the methanol was evaporated and the mixture was extracted with ethyl acetate. The aqueous layer was acidified to pH 3–3.4 and evaporated to dryness in vacuum. The dry solid residue was reconstituted with minimal amount of cold acidic (pH 3) water to dissolve inorganics and filtered to afford, after washing with ethyl acetate and drying, 0.62 g (87%) of (1R*,2R*,3R*,4S*6S*)-3-(4-fluorobenzyl)amino-tricyclo [2.2.1.0$^{2,6}$]heptane-1,3-dicarboxylic acid.

A solution of 0.31 g (1.0 mmol) of the latter in 20 mL of methanol was subjected to hydrogenolysis by hydrogen in the presence of 10% palladium on carbon at room temperature and atmospheric pressure for 36 hours. After the reaction was complete, the catalyst was removed by filtration and washed several times with boiling water to yield, after removal of solvents in vacuum, 0.19 g (97%) of the title compound. m.p.>260° C., $[\alpha]_{25}^D = -10.5°$ (measured in water).

Elemental analysis for: $C_9H_{11}NO_4 \cdot 1\ H_2O$.
Calc'd: C, 50.18; H, 6.04; N, 6.51
Found: C, 50,07; H, 5.45; N, 6.32

The second enantiomer to elute from chiral HPLC column (intermediate (4')) was converted in an analogous manner into (+)-(1R*,2R*,3R*,4S*,6S*)-3-aminotricyclo[2.2.1.0$^{2,6}$]heptane-1,3-dicarboxylic acid. M. p.>260° C.; MS, (−) ESI, [M−H]$^−$=196; $[\alpha]_{25}^D = +9.6°$ (measured in water).
Elemental analysis for $C_9H_{11}NO_4\ 0.75\ H_2O$
Calculated: C, 51.30; H, 5.93; N, 6.65
Found: C, 51.22; H, 5.36; N, 6.61

EXAMPLE 4

(1S*,2R*,4S*,6S*)-N-[(1R)-1-benzyl-2-hydroxyethyl]-3-oxotricyclo[2.2.1.0$^{2,6}$]-heptane-1-carboxamide; and

EXAMPLE 5

(1R*,2S*,4R*,6R*)-N-[(1R)-1-benzyl-2-hydroxyethyl]-3-oxotricyclo[2.2.1.0$^{2,6}$]-heptane-1-carboxamide;

A mixture of 3-oxotricyclo[2.2.1.0$^{2,6}$]heptane-1-carboxylic acid (0.3 g, 1.946 mmole, prepared according Chem.Ber., GE, 93, 1960, 2271–2281), R-(+)2-amino-3-phenyl-1-propanol (0.324 g, 2.141 mmole) and 4-methylmorpholine (0.86 mL, 7.784 mmole) in dimethylformamide (7 mL) was stirred at ambient temperature. 2-(1H-Benzotriazol-1-yl)-1,1,3,3-tetra-methyluronium tetrafluoroborate (TBTU, 0.75 g, 2.335 mmole) was added to the reaction mixture and stirring was continued for 18 hours. The reaction mixture was diluted with ethyl acetate (35 mL), the organic layer separated, washed with 5% aqueous citric acid (2×30 mL), followed by saturated NaHCO$_3$ solution (2×30 mL), and finally washed with brine (50 mL). The organic layer was dried over magnesium sulfate, filtered and evaporated to dryness. Using a reversed phase HPLC (C-18, 8 μM particle size, 41.4 mm and 4.6 mm ID, 25 cm L) column, 10–70% CH$_3$CN/Water, both diastereomers were isolated as light yellow oils in 60% yield. The retention times for the diastereomers A and B were 15.3 min. and 15.8 min., respectively.

A: MS (EI, M$^+$ @ m/z) 285
B: MS (APCI, [M+H]$^+$ @ m/z) 286

EXAMPLE 6

Spiro-hydantoin diastereomers of (1S*,2R*,4S*,6S*)-N-[(1R)-1-benzyl-2-hydroxy-ethyl]-3-oxotricyclo[2.2.1.0$^{2,6}$]heptane-1-carboxamide A mixture of (1S,2R,4S,6S)-N-[(1R)-1-benzyl-2-hydroxyethyl]-3-oxotricyclo-[2.2.1.0$^{2,6}$]heptane-1-carboxamide (A, 0.63 g, 2.207 mmole), ammonium carbonate (1.048 g, 10.091 mmole) and potassium cyanide (0.173 g, 2.648 mmole) was stirred in methanol/water (2:1, 15 ml) at 50° C. for 72 hours. After evaporation of the solvent in vacuo the products were isolated using reversed phase HPLC (C-18, 8 μm particle size, 41.4 mm and 4.6 mm ID, 25 cm L) column, 10–70% CH$_3$CN/water. Both diastereomers were isolated in 31% yield (C) and 53% yield (D) as white solids; mp's A, >260° C. (Decomposition) and B, 167–9° C. The retention times for the diastereomers C and D was 12.6 min. and 13.7 min., respectively.

C: MS (+APCI, [M+H]$^+$ @ m/z) 356
D: MS (+APCI, [M+H]$^+$ @ m/z) 356

EXAMPLE 7

Spiro-hydantoin diastereomers of (1R*,2S*,4R*,6R*)-N-[(1R)-1-benzyl-2-hydroxy-ethyl]-3-oxotricyclo [2.2.1.0$^{2,6}$]heptane-1-carboxamide A mixture of (1R,2S,4R,6R)-N-[(1R)-1-benzyl-2-hydroxyethyl]-3-oxotricyclo-[2.2.1.0$^{2,6}$]heptane-1-carboxamide (B, 0.52 g, 1.822 mmole), ammonium carbonate (0.9 g, 9.366 mmole) and potassium cyanide (0.142 g, 2.186 mmole) was stirred in methanol/water (2:1, 15 ml) at 50° C. for 72 hours. After evaporation of the solvent in vacuo the products were isolated using reversed phase HPLC (C-18, 8 μm particle size, 41.4 mm and 4.6 mm ID, 25 cm L) column, 10–70% CH$_3$CN/water. Both diastereomers were isolated in 34% yield (E) and 76% yield (F) as white solids; mp's E, 270–2° C. (Decomposition) and F, 80–2° C. The retention times for the diastereomers E and F were 14.7 min. and 15.3 min., respectively.

E: MS (+APCI, [M+H]$^+$ @ m/z) 356
F: MS (+APCI, [M+H]$^+$ @ m/z) 356

General Procedure for the Preparation of all Four Stereoisomers of 3-amino-tricyclo[2.2.1.0$^{2,6}$] heptane-1,3-dicarboxylic acid A mixture of the starting spiro-hydantoin-N-[(1R)-1-benzyl-2-hydroxyethyl]-3-oxotricyclo [2.2.1.0$^{2,6}$]heptane-1-carboxamide (0.5 mmole) and 2N NaOH (3 mL) was refluxed for 20 hours. The reaction mixture was cooled to ambient temperature and washed with dichloromethane (2×20 mL). The aqueous layer was separated and the pH adjusted to 11 using 10% aqueous acetic acid and eluted through an ion-exchange column (Bio-Rad AG1-X8 resin, acetate form, 100–200 mesh). The products were eluted with 1M acetic acid and the combined fractions were collected and concentrated on a lyophilizer to give the desired stereoisomers as white solids.

EXAMPLE 8

(−)-(1R*,2R*,3R*,4S*,6S*)-3-Aminotricyclo [2.2.1.0$^{2,6}$]heptane-1,3-dicarboxylic acid Yield: 98%; MS (APCI, [M+H]$^+$ @ m/z) 198; mp>260° C. (Decomposition); Optical Rotation (water & NaOH) $[\alpha\text{-D}]^{25} = -32.1°$

EXAMPLE 9

(+)-(1R,2R,3R,4S,6S)-3-Aminotricyclo[2.2.1.0$^{2,6}$] heptane-1,3-dicarboxylic acid Yield: 45%; MS (APCI, [M−H]$^+$ @ m/z) 196; mp>260° C. (Decomposition); Optical Rotation (water & NaOH) $[\alpha\text{-D}]^{25} = +31.01°$

EXAMPLE 10

(+)-(1R*,2S*,3R*,4R*,6S*)-3-Aminotricyclo[2.2.1.0$^{2,6}$]heptane-1,3-dicarboxylic acid Yield: 51%; MS (APCI, [M–H]$^+$ @ m/z) 196; mp>280° C. (Decomposition); Optical Rotation (water & NaOH) [α–D]$^{25}$=+23.98°

EXAMPLE 11

(−)-(1R*,2S*,3S*,4R*,6R*)-3-Aminotricyclo[2.2.1.0$^{2,6}$]heptane-1,3-dicarboxylic acid Yield: 50%; MS (APCI, [M–H]$^+$ @ m/z) 196; mp>260° C. (Decomposition); Optical rotation (water & NaOH) [α–D]$^{25}$=−16.0°

What is claimed:

1. A compound of the formula:

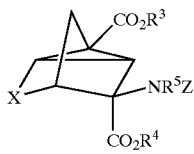

wherein:
X is $(CH_2)_n$, O, S, SO, $SO_2$ or $CR^1R^2$;
n is 1 or 2;
$R^1$ and $R^2$ are, independently, hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;
$R^3$, $R^4$ and $R^5$ are, independently, hydrogen or alkyl of one to six carbon atoms;
Z is hydrogen, alkyl of one to six carbon atoms, alkanoyl of one to six carbon atoms or alkoxycarbonyl of two to seven carbon atoms;
or a pharmaceutically acceptable salt thereof.

2. A compound of claim 1 wherein:
$R^1$, $R^2$ and n are as defined in claim 1;
X is $(CH_2)_n$, O or $CR^1R^2$;
$R^3$, $R^4$ and $R^5$ are hydrogen; and
Z is hydrogen or alkyl of one to six carbon atoms;
or a pharmaceutically acceptable salt thereof.

3. A compound of claim 2 wherein:
X is $(CH_2)_n$, O or $CR^1R^2$;
$R^1$ and $R^2$ are independently selected from hydrogen, halogen, hydroxy, alkyl of one to six carbon atoms or alkoxy of one to six carbon atoms; and
$R^3$, $R^4$, $R^5$ and Z are hydrogen;
or a pharmaceutically acceptable salt thereof.

4. A compound of the formulae:

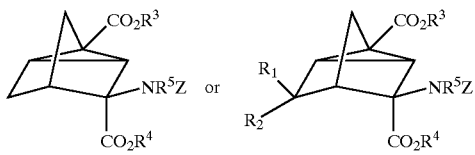

wherein:
$R^1$ and $R^2$ are independently selected from hydrogen, halogen, hydroxy, alkyl of one to six carbon atoms, alkoxy of one to six carbon atoms, or $R^1$ and $R^2$, taken together with the carbon to which they are attached, form cycloalkyl of three to six carbon atoms, an alkylidene of up to six carbon atoms or a carbonyl;
$R^3$, $R^4$ and $R^5$ are, independently, hydrogen or alkyl of one to six carbon atoms;
Z is hydrogen, alkyl of one to six carbon atoms, alkanoyl of one to six carbon atoms or alkoxycarbonyl of two to seven carbon atoms;
or a pharmaceutically acceptable salt thereof.

5. A compound of claim 4 having the formulae:

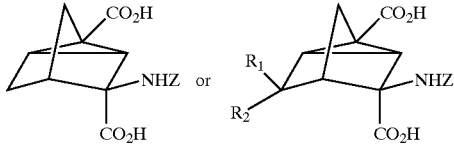

wherein:
Z is H or alkyl of from 1 to 6 carbon atoms; and
$R_1$ and $R_2$ are independently selected from H, halogen, hydroxy, alkyl of from 1 to 6 carbon atoms or alkoxy of from 1 to 6 carbon atoms;
or a pharmaceutically acceptable salt thereof.

6. A compound of claim 4 selected from the group of:
3-Amino-tricyclo[2.2.1.0$^{2,6}$]heptane-1,3-dicarboxylic acid;
3-Methylamino-tricyclo[2.2.1.0$^{2,6}$]heptane-1,3-dicarboxylic acid;
3-Ethylamino-tricyclo[2.2.1.0$^{2,6}$]heptane-1,3-dicarboxylic acid;
3-Amino-5-methyl-tricyclo[2.2.1.0$^{2,6}$]heptane-1,3-dicarboxylic acid;
3-Amino-5-chloro-tricyclo[2.2.1.0$^{2,6}$]heptane-1,3-dicarboxylic acid;
3-Amino-5-bromo-tricyclo[2.2.1.0$^{2,6}$]heptane-1,3-dicarboxylic acid;
3-Amino-5,5-dichloro-tricyclo[2.2.1.0$^{2,6}$]heptane-1,3-dicarboxylic acid;
3-Amino-5,5-dichloro-tricyclo[2.2.1.0$^{2,6}$]heptane-1,3-dicarboxylic acid;
5,5-Dimethyl-3-methylamino-tricyclo[2.2.1.0$^{2,6}$]heptane-1,3-dicarboxylic acid;
5-Hydroxy-3-methylamino-tricyclo[2.2.1.0$^{2,6}$]heptane-1,3-dicarboxylic acid;
3-Amino-5-methoxy-tricyclo[2.2.1.0$^{2,6}$]heptane-1,3-dicarboxylic acid;
5-Methoxy-3-methylamino-tricyclo[2.2.1.0$^{2,6}$]heptane-1,3-dicarboxylic acid;
or a pharmaceutically acceptable salt thereof.

7. A compound of the formula:

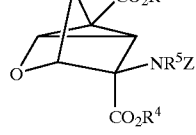

wherein:
$R^3$, $R^4$ and $R^5$ are independently selected from hydrogen or alkyl of one to six carbon atoms; and
Z is hydrogen, alkyl of one to six carbon atoms, alkanoyl of one to six carbon atoms or alkoxycarbonyl of two to seven carbon atoms;
or a pharmaceutically acceptable salt thereof.

8. A compound of claim 7 of the formula:

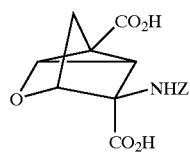

wherein Z is selected from H or alkyl of from 1 to 6 carbon atoms; or a pharmaceutically acceptable salt thereof.

9. A compound of claim 1 which is (1R*,2R*,3R*,4S*,6S*)-3-amino-tricyclo[2.2.1.0$^{2,6}$]heptane-1,3-dicarboxylic acid or a pharmaceutically acceptable salt thereof.

10. A compound of claim 1 which is (1R*,2R*,3S*,4S*,6S*)-3-amino-tricyclo[2.2.1.0$^{2,6}$]heptane-1,3-dicarboxylic acid or a pharmaceutically acceptable salt thereof.

11. A compound of claim 1 which is (−)-(1R*,2R*,3R*,4S*,6S*)-3-amino-tricyclo[2.2.1.0$^{2,6}$]heptane-1,3-dicarboxylic acid or a pharmaceutically acceptable salt thereof.

12. A compound of claim 1 which is (−)-(1R*,2R*,3R*,4S*,6S*)-3-Aminotricyclo[2.2.1.0(2,6)] heptane-1,3-dicarboxylic acid, or a pharmaceutically acceptable salt form thereof.

13. A compound of claim 1 which is (+)-(1R*,2R*,3R*,4S*,6S*)-3-Aminotricyclo[2.2.1.0(2,6)] heptane-1,3-dicarboxylic acid, or a pharmaceutically acceptable salt form thereof.

14. A compound of claim 1 which is (+)-(1R,2S,3R,4R,6S)-3-Aminotricyclo[2.2.1.0(2,6)] heptane-1,3-dicarboxylic acid, or a pharmaceutically acceptable salt form thereof.

15. A compound of claim 1 which is (−)-(1R,2S,3S,4R,6R)-3-Aminotricyclo[2.2.1.0(2,6)] heptane-1,3-dicarboxylic acid, or a pharmaceutically acceptable salt form thereof.

16. A method of treatment in a mammal of a disease of brain glutamate hypofunction, the method comprising administering to a mammal in need thereof a pharmaceutically effective amount of a compound of claim 1, or a pharmaceutically acceptable salt thereof.

17. The method of claim 16 wherein the disease of brain glutamate hypofunction is selected from the group of schizophrenia, schizoaffective disorder or schizophreniform disorder.

18. A pharmaceutical composition comprising a pharmaceutically effective amount of a compound of claim 1, or a pharmaceutically acceptable salt thereof, and a pharmaceutically acceptable carrier or excipient.

* * * * *